(12) United States Patent
Roa-Espinosa et al.

(10) Patent No.: US 8,907,113 B2
(45) Date of Patent: Dec. 9, 2014

(54) ENHANCED BIODIESEL PROCESS

(76) Inventors: Aicardo Roa-Espinosa, Madison, WI (US); Hailin Lin, Guangzhou (CN)

(*) Notice: Subject to any disclaimer, the term of this patent is extended or adjusted under 35 U.S.C. 154(b) by 249 days.

(21) Appl. No.: 13/539,454

(22) Filed: Jul. 1, 2012

(65) Prior Publication Data

US 2012/0277461 A1  Nov. 1, 2012

Related U.S. Application Data

(63) Continuation-in-part of application No. 12/509,450, filed on Jul. 25, 2009, now abandoned.

(51) Int. Cl.

| | | |
|---|---|---|
| C11C 3/00 | (2006.01) |
| C07C 67/03 | (2006.01) |
| C11C 3/04 | (2006.01) |
| C07C 67/02 | (2006.01) |
| C11C 1/10 | (2006.01) |
| C07C 29/76 | (2006.01) |
| C11B 3/00 | (2006.01) |
| C11B 3/06 | (2006.01) |

(52) U.S. Cl.
CPC . *C07C 67/03* (2013.01); *C11C 3/04* (2013.01); *C07C 67/02* (2013.01); *C11C 1/10* (2013.01); *C11C 3/003* (2013.01); *Y02E 50/13* (2013.01); *C07C 29/76* (2013.01); *C11B 3/001* (2013.01); *C11B 3/06* (2013.01)
USPC .......................................... 554/169; 554/124

(58) Field of Classification Search
None
See application file for complete search history.

(56) References Cited

U.S. PATENT DOCUMENTS

| | | | | |
|---|---|---|---|---|
| 4,668,439 | A | * | 5/1987 | Billenstein et al. ........... 554/167 |
| 4,695,411 | A | * | 9/1987 | Stern et al. .................... 554/167 |
| 5,976,357 | A | * | 11/1999 | Strom et al. .................. 208/184 |
| 6,767,460 | B1 | * | 7/2004 | Clough ....................... 210/502.1 |
| 6,884,900 | B2 | | 4/2005 | Maeda |
| 7,045,100 | B2 | | 5/2006 | Ergun |
| 7,087,771 | B2 | | 8/2006 | Luxem |
| 7,138,536 | B2 | | 11/2006 | Bournay |
| 2005/0274065 | A1 | | 12/2005 | Portnoff |
| 2006/0110521 | A1 | * | 5/2006 | Heise et al. ................... 426/601 |
| 2006/0293533 | A1 | | 12/2006 | Iyer |
| 2007/0004599 | A1 | | 1/2007 | Darbha |
| 2007/0033863 | A1 | | 2/2007 | Butler |

FOREIGN PATENT DOCUMENTS

JP  2004307608  * 11/2004  ................ C10L 1/02

OTHER PUBLICATIONS

JP 2004-307608, Sekiguchi, Y. et al., Producitn Medhod of diesel fuen oil form waste fat and oil, 2004, English translation, 14 pages.*

(Continued)

*Primary Examiner* — Yate K Cutliff
(74) *Attorney, Agent, or Firm* — Steven H. Greenfield; Greenfield Invention and Patent Consulting Inc

(57) ABSTRACT

A process for separating glycerin from methyl ester at an enhanced rate is disclosed. The improved process results from carrying out the transesterification reaction in a substantially non-polar and water free environment. A polymer selected from a group of polymers shown to be effective in such an environment is added to the product mixture which greatly improves the rate of separation between the methyl ester and the glycerin and reduces the number of required steps to accomplish the separation.

19 Claims, 3 Drawing Sheets

(56) References Cited

OTHER PUBLICATIONS

Ma, F. et al., Biodiese production: a reiview, 1999, Bioresource technology, No. 70, pp. 1-15.*

Freedman, B. et al., Variable affecting the yields of fatty esters from transesterified vegetable oils, 1984, JAOCS, vol. 61, No. 10, pp. 1638-1643.*

Biodiesel expert, Purolite, 2008, 2 pages.*

* cited by examiner

ENHANCED BIODIESEL PROCESS

RELATED APPLICATIONS

This application is a continuation in part of non-provisional application Ser. No. 12/509,450 filed on Jul. 25, 2009.

FIELD OF THE INVENTION

The present invention relates to a method of manufacturing biodiesel. More specifically it concerns modifications to process conditions that enhance the speed at which the two major products of the reaction, glycerin and methyl ester are separated and allow the process to be carried out in fewer steps than in the current art.

DESCRIPTION OF PRIOR ART

The term biodiesel typically refers to any diesel fuel substitute derived from renewable sources such as vegetable oils or animal fats. Biodiesel is frequently mixed with petroleum diesel for use as a vehicle fuel.

The most common process for the production of biodiesel involves the reaction of triesters or triglycerides with an alcohol in the presence of a catalyst referred to as transesterification. The triglycerides used in the reaction may originate from sources including but not limited to 1) animal fat such as beef tallow, 2) vegetable oils such as rapeseed, corn, sunflower, soybean, coconut, canola, cottonseed, palm seed, mustard seed, and 3) recycled sources such as restaurant waste frying oils, and industrial waste grease. The alcohol is most typically methanol, but ethanol may be used as well. The products of the reaction are methyl ester and glycerin also referred to in the art as glicerine or glycerol. The catalysts most commonly used are sodium or potassium hydroxide and the reaction is carried out at a pH between about 8.5 and 9.5. Sodium hydroxide reacts with methanol to produce sodium methylate $NaOCH_3$ which acts as a catalyst in the reaction to produce methyl ester and glycerin.

The reaction between triglyceride and methanol produces methyl ester generally known in the art as biodiesel, having a general formula of:

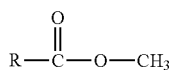

where R is generally an alkyl group of about 15 to about 20 carbons. In the specific example below, the triglyceride molecule contains three different R groups ($R_1$, $R_2$ and $R_3$). The reaction of this molecule with the methanol and sodium hydroxide catalyst thus results in three methyl ester molecules, each having a different R group. In other embodiments, however, the R groups may be all the same or two of the three may be the same.

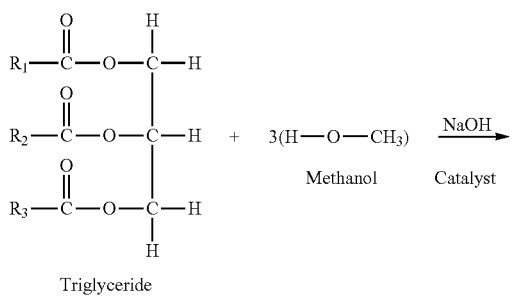

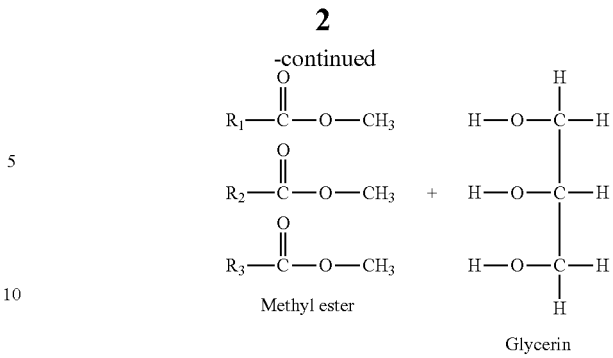

Typically, about one unit of weight of glycerin is produced for every ten units of weight of methyl ester. It is desirable to remove any water from the feed source and to minimize free fatty acid content as excess water and fatty acids produce side reactions that reduce the efficiency and yield of the biodiesel. Methyl esters react with water to produce fatty acids and methanol, and fatty acids react with sodium methylate to produce soap and methanol as shown below. Soap is an undesirable by-product of the reaction and must be separated and removed.

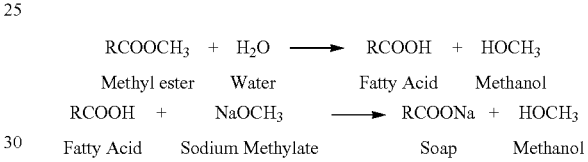

The rate of transesterification reaction is strongly dependent on temperature. At ambient temperatures, about 4-8 hours are required to complete the reaction. At 40° C., about 2-4 hours are required, while at 60° C., the reaction can be completed in about 1-2 hours. While it may be desirable to further reduce reaction time by increasing the reaction temperature, this may be impractical since methanol boils at about 65° C., and carrying out the reaction at 70° C. or above may be deemed unsafe due to fire and explosion risks.

The biodiesel production process generally is designed for the following sequence of steps:
 a. Pre-treating the feed source containing triglyceride,
 b. Heating the pretreated feed source to the desired reaction temperature,
 c. Reacting the feed source with methanol and a catalyst,
 d. Recovering the methanol by distillation and reusing the recovered methanol in subsequent biodiesel production steps,
 e. Separating the glycerin from the biodiesel and recovering the biodiesel fraction and the glycerin fraction,
 f. Washing the biodiesel fraction with a weak and dilute acid solution to neutralize the excess caustic and decanting the wash solution,
 g. Washing the biodiesel fraction with water to remove soap followed by decanting the wash water, and
 h. Distilling off excess water not removed by decanting.

Feed source pretreatment can include filtration, dehydration, degumming, de-acidification and bleaching depending on whether the feed source is predominantly vegetable oil or recycled oil and fat. The purpose of the pretreatment is to reduce the free fatty acids in the feed source to about 0.5% or less.

An example of a reactant mixture disclosed in the art is about 0.5% by weight of the feed source of sodium hydroxide (NaOH) and 1 mole of the feed per 3 moles of methanol. Alternatively, the catalyst is potassium hydroxide (KOH).

The transesterification reaction time is 2 hours at 60° C. and the reaction is carried out at a pH of between about 8.5 and about 9.5. Methanol distillation is carried out at about 65° C. The acid wash is done using a weak acid such as acetic acid, carbonic acid, citric acid or phosphoric acid. Water is boiled off in the last step at about 120° C.

An alternative sequence may be to carry out the separation of glycerin and methyl ester step before the methanol distillation step. With this sequence, the separation of the biodiesel fraction is followed by distilling off the methanol from the biodiesel fraction, which in turn is followed by washing the biodiesel to remove soap and other impurities. The methanol is then distilled off the glycerin fraction, and the methanol distilled from the two fractions is combined and dehydrated. Finally, the recovered methanol is recycled back into the biodiesel reactor.

Acid and water washing remove impurities from the methyl ester including residual soaps, excess methanol, residual lye, free glycerin and other contaminants that are detrimental to the quality of the fuel and can adversely affect engine performance.

Biodiesel produced primarily from soybean oil and animal fats is commonly blended with diesel fuel up to 20% for use in diesel powered engines. In some engines, fuel blends comprising biodiesel contents higher than 20% are used.

The separation of glycerin from the methyl ester can be accomplished by allowing the glycerin, which is thicker and heavier than methyl ester, to settle. The settling of glycerin can take from several hours to a full day. A multitude of methods used for speeding up glycerin separation are disclosed in prior art patents and publications. These include microwave treatment, use of catalysts, centrifuging, filtration through membranes, and ultrasonic irradiation. Pre-grant publication No 20050274065 discloses methods for producing biodiesel transesterification, esterification, and esterification-transesterification (both one-step and two-step) for producing biofuels. The process may be enhanced by one or more of the following: 1) applying microwave or RF energy; 2) passing reactants over a heterogeneous catalyst at sufficiently high velocity to achieve high shear conditions; 3) emulsifying reactants with a homogeneous catalyst; or 4) maintaining the reaction at a pressure at or above autogeneous pressure. Pre-grant publication No. 20070033863 teaches methods of producing biofuels from trap grease. Systems and apparatus also are provided for implementing, for example and without limitation, the methods described herein. Pre-grant publication No. 20070004599 provides an improved process for the preparation of lubricants from vegetable oil or fat obtained from animal source. The present invention involves a reaction of vegetable oil or fat with an alcohol in the presence of a double metal cyanide catalyst, at a temperature in the range of 150 degrees to 200 degree C. for a period of 3-6 hrs to obtain the desired bio-lubricant. Pre-grant publication No. 20060293533 is directed to esterification, and transesterification of fats and oils is conducted using one or more heterogeneous solid catalysts in the presence of an alcohol and a cosolvent. In one example, esterification of free fatty acids in fats and oils feedstock is conducted by contacting the feedstock with a solid catalyst having acidic groups. Transesterification of triglyceride in the feedstock is conducted by contacting the feedstock with a solid catalyst having basic groups. The disclosure further describes ester separation from the by product glycerol using a centrifuge, gravity settling or another equivalent technique, and the ester phase is water washed to obtain high purity esters. U.S. Pat. No. 7,138,536 describes a process for producing fatty acid alkyl esters and glycerol comprising at least one reaction stage in which a charge comprising a vegetable and/or animal oil and an alcohol are brought into contact in the presence of a heterogeneous catalyst, so as to obtain an effluent comprising at least alkyl esters, glycerol and alcohol, and at least one separation stage during which a separation is carried out of at least one portion of the effluent so as to separate an alcohol-rich effluent and an alkyl esters-rich effluent, at least one separation stage consists of a membrane separation using at least one alcohol-permeable membrane. U.S. Pat. No. 7,045,100 describes a method for producing fatty acid methyl ester, including compounding saturated and unsaturated higher fatty substances from at least one of vegetable and animal with an alkaline solution dissolved in alcohol to form a mixture. The method also includes emulsifying the mixture to reach a chemical balance state in a reaction section, wherein fats are transesterified into fatty acid methyl ester, wherein border surfaces of the mixture are enlarged by dynamic turbulence in the reaction section and the transesterification is performed under pressure, and wherein the pressure is reduced during transesterification. U.S. Pat. No. 6,884,900 provides a method for producing a fatty acid alcohol ester useful as a substitute fuel for light oil in which an ester interchange reaction between fats or oils and alcohol is carried out in a reactor by applying ultrasonic irradiation at a frequency of 15 to 100 kHz and irradiation intensity of 0.5 to 20 W/cm$^2$ in the presence of a catalyst, followed by an application of ultrasonic irradiation at a frequency of 200 to 3,000 kHz and irradiation intensity of 0.5 to 20 W/cm$^2$ to the reaction product in a separation tank 4 to separate fatty acid alcohol ester and glycerol. Such ultrasonic irradiation in the separation tank may be applied to an interface between fatty acid alcohol ester and glycerol. U.S. Pat. No. 7,087,771 refers to a method for making alkyl esters (e.g., methyl ester), such as biodiesel, from an oil source. The method involves converting the free fatty acids of the oil source into a mixture of mono-, di-, and tri-glycerides and subsequently transesterifying the newly formed glycerides as well as the originally present glycerides into fatty acid alkyl esters.

SUMMARY OF THE PRESENT INVENTION

The object of the present invention is a process for the separation of the methyl ester from glycerin carried out at an enhanced rate and reduced number of process steps compared to the current art.

The method of the present invention for producing methyl ester comprises: providing a feed source containing triglyceride; blending an alcohol and a catalyst with the feed source to produce a reactant mixture comprising of alcohol, pretreated feed source and catalyst; heating the reactant mixture to a predetermined reaction temperature; reacting the reactant mixture for a predetermined reaction time to produce a product mixture comprising of methyl ester, glycerin, alcohol and catalyst; blending a polymer with the product mixture; heating the product mixture to a predetermined separation temperature; separating a glycerin fraction from a methyl ester fraction; recovering the methyl ester fraction; and recovering the glycerin fraction.

It is noted that the process is carried out in a substantially water free and non-polar environments as the presence of water has a hindering effect on the speed of separation. Thus only specific polymers that can act to enhance the separation of glycerin from the methyl ester in a substantially water free and non-polar environment are suitable for this process. While small and incidental amounts of water may be introduced with the process reactants, it is desirable, that the percent water in the reaction phase be less than 1% and preferably less than 0.1% by weight. Such small amounts may originate from ambient moisture or present in the polymers that are added in amounts not exceeding 25 ppm.

These and other features, aspects and advantages of the present invention will become better understood with reference to the following drawings, description and claims.

DETAILED DESCRIPTION OF THE INVENTION

Figure 1:
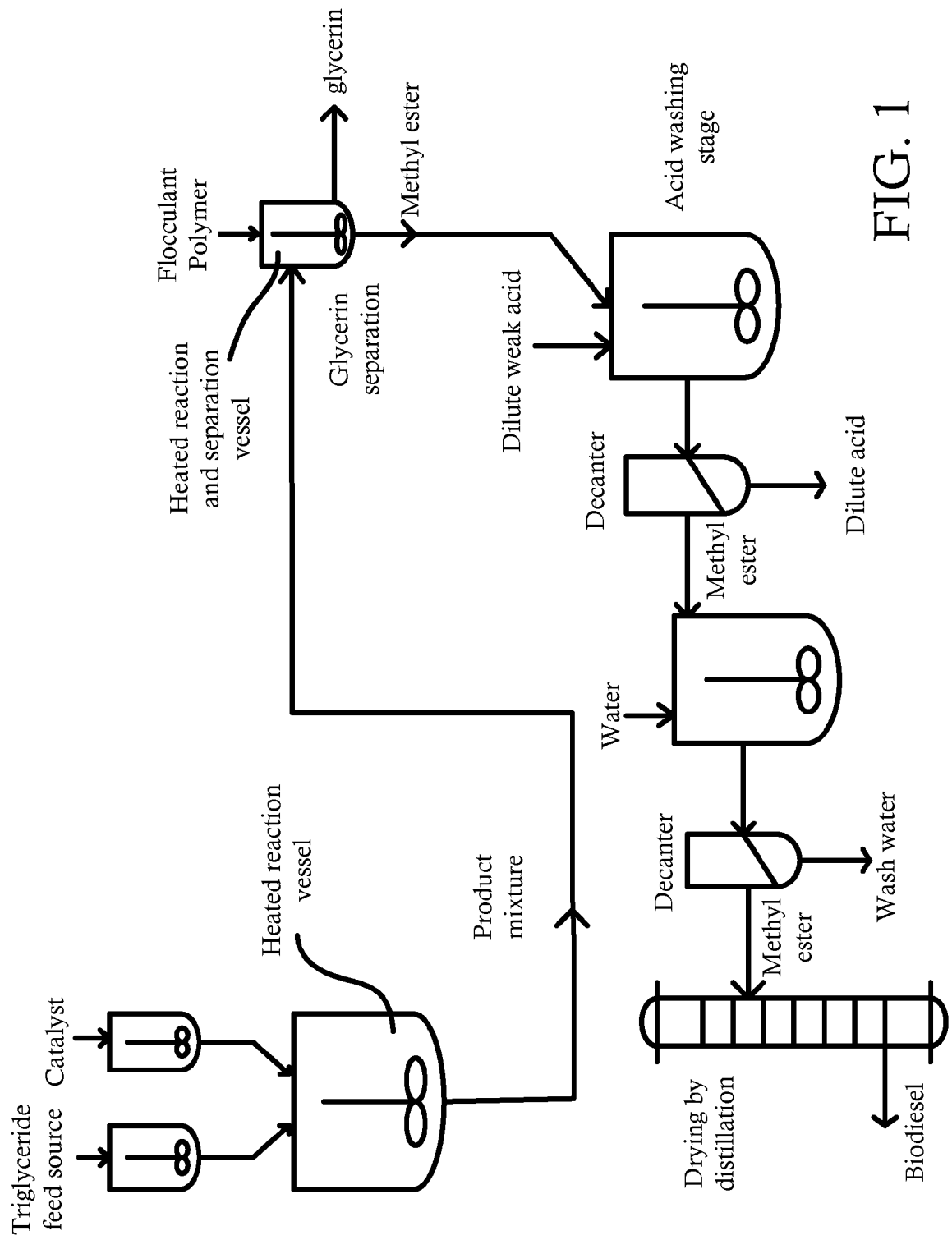
FIG. 1 is a schematic of a biodiesel process according to an embodiment of the present invention.

It is the object of the present invention to provide a process of separating the glycerin from methyl ester that is more effective and one that is significantly faster than that achievable in the current art without the need of additional equipment or steps such as microwave treatment, catalysis, centrifuging, filtration through membranes, and ultrasonic irradiation.

An embodiment of the biodiesel production process of the present invention comprises blending a polymer with the mixture of the products of the reaction at an amount of about 0.5 parts per million to about 100 parts per million by the weight of the feed source, and preferably between about 5 parts per million to about 25 parts per million by the weight of the feed source. An exemplary embodiment for a specific process sequence is as follows:

1. Providing a triglyceride feed source that may contain oil from varied sources including animal fat such as beef tallow, vegetable oils such as rapeseed, corn, sunflower, soybean, coconut, canola, cottonseed, palm seed, mustard seed, and recycled sources such as restaurant waste frying oils, and industrial waste grease, 2. Heating the triglyceride feed source to a predetermined reaction temperature, 3. Reacting the pre-treated feed source with methanol and a catalyst at the reaction temperature to produce a products mixture of methyl ester, glycerin, and residual methanol and catalyst. The product mixture may also contain impurities that are either contained in the oil feed source or are byproducts of the reaction such as residual soaps, excess methanol, residual lye, water and free fatty acids, 4. Blending a polymer with the products mixture at an amount of about 0.5 parts per million to about 100 parts per million by the weight of the pretreated feed source, and more preferably between about 5 parts per million to about 25 parts per million, 5. Heating the product mixture and polymer to a temperature conducive for separating the glycerin from the methyl ester, and 6. Precipitating the glycerin and separating the glycerin fraction from the methyl ester fraction. In this embodiment of the present invention, most of the excess un-reacted methanol is contained in the glycerin fraction.

The reaction may take place in a temperature range between about 25° C. to about 50° C., but preferably in the temperature range of about 35° C. to about 45° C. for a time ranging from about 20 minutes to about 60 minutes. The catalyst may be sodium hydroxide or potassium hydroxide added to achieve a pH of the reactant mixture of between about 8.5 and about 9.5. The methanol is typically added in excess over the stoichiometric amount of three moles of methanol to one mole of triglyceride to speed up the reaction.

In another embodiment of the present invention, the triglyceride source is pretreated by processes known in the art including dehydration, filtration, degumming, de-acidification and bleaching depending on whether the feed source is predominantly vegetable oil or recycled oil and fat. Pretreatment of the triglyceride source may also be accomplished by blending a polymer with the triglyceride source and precipitating and removing impurities present in the triglyceride source. An exemplary process for pretreating the triglyceride source in this manner comprises: heating the triglyceride source to a temperature in a range of between about 25° C. to about 35° C.; blending an amount of a caustic solution ranging from about 0.2% to about 2% by weight with the triglyceride source and mixing the triglyceride source with the caustic solution for at least 10 minutes; heating the blend of the triglyceride source and caustic solution to a temperature ranging from between about 40° C. to about 70° C.; adding an amount of a polymer to the blend of the triglyceride source and caustic solution ranging between about 1 parts per million and about 25 parts per million of the triglyceride source; mixing the blend of the triglyceride source and caustic solution with the polymer for an amount of time ranging between about 2 minutes and 15 minutes to achieve a well dispersed blend of the triglyceride source, caustic solution and polymer; precipitating an impurities residue layer from the a refined triglyceride layer; and separating the impurities residue layer from the refined triglyceride layer.

The glycerin precipitation temperature may range from about 40° C. to about 80° C., and more preferably between about 60° C. to about 70° C. To precipitate the glycerin, the products mixture and the polymer are allowed to settle for a time ranging from about two hours and four hours.

The polymer is selected from the group consisting of sodium acrylate acrylamide copolymer, polydimethylamine-epichlorohydrin, polydicyandiamide, diallyldimethyl-ammonium chloride, poly-diallyldimethyl-ammonium chloride (Poly-DADMAC), or combinations thereof.

Alternate embodiments of the biodiesel process may additionally include any one of the following steps as needed or desired:

a. Recovering the methanol from the products mixture by distilling the product mixture and reusing the recovered methanol in subsequent biodiesel production steps, b. Washing the biodiesel fraction with a weak and dilute acid solution to neutralize the excess caustic and removing the wash solution by decanting, c. Washing the biodiesel fraction with water to remove soap followed by removing the wash water by decanting, and d. Distilling off excess water not removed by decanting.

The methanol distillation step may be carried out from the products mixture before blending the polymer or after blending the polymer with the products mixture.

The separation of glycerin from the biodiesel is done under this sequence by gravity as the glycerin, which is heavier than the biodiesel, precipitates to the bottom of the holding tank. The acid wash is accomplished using a weak acid. Weak acids suitable for this purpose include citric acid, carbonic acid, phosphoric acid and acetic acid.

In one embodiment of the present invention, the polymer is polydicyandiamide (DMD), a branched polyamine. Polydicyandiamide is obtained from the reaction of dicyandiamide monomer and formaldehyde as shown below:

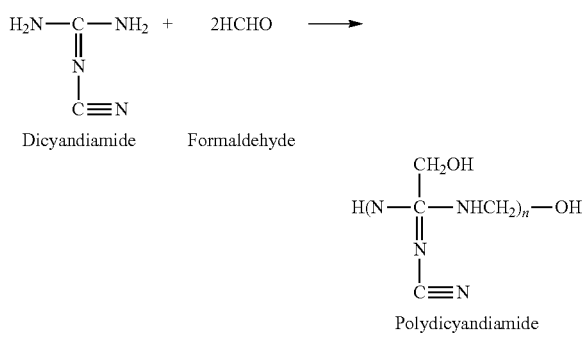

Dicyandiamide   Formaldehyde

Polydicyandiamide

In this embodiment, the molecular weight of the Polydicyandiamide is between about 3000 and 150,000 and it has a high cationic charge level.

In another embodiment of the present invention, the polymer is polydimethylamine-epichlorohydrin which is a linear cationic polyamine obtained from the reaction of dimethylamine and epichlorohydrin:

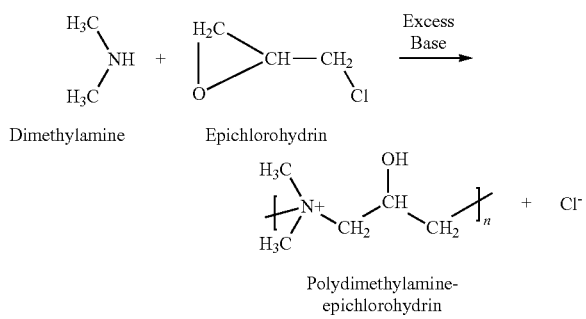

Dimethylamine   Epichlorohydrin

Polydimethylamine-epichlorohydrin

The molecular weight of the polydimethylamine-epichlorohydrin is ideally between about 10,000 and 1,000,000.

In yet another embodiment of the present invention, the polymer is diallyldimethyl-ammonium chloride (DADMAC), or poly-diallyldimethyl-ammonium chloride (Poly-DADMAC), a cationic branched polyamine that is a product of the reaction between dimethylamine and allyl chloride. Diallyldimethyl-ammonium chloride and poly-diallyldimethyl-ammonium chloride are produced by the same reaction shown below, but diallyldimethyl-ammonium chloride is made under conditions that inhibit polymerization while the poly-diallyldimethyl-ammonium chloride is made under conditions that promote polymerization. The molecular weight of the poly-diallyldimethyl-ammonium chloride is ideally between about 10,000 and 1,000,000.

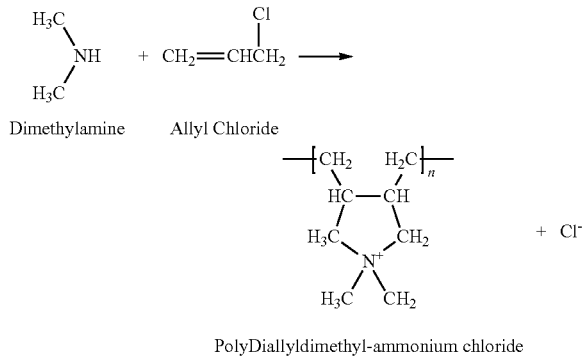

Dimethylamine   Allyl Chloride

PolyDiallyldimethyl-ammonium chloride

In yet another embodiment of the present invention, the polymer is sodium acrylate acrylamide copolymer. This polymer may be made from the reaction between an acrylamide monomer and an acrylic acid monomer as shown below. The sodium acrylate acrylamide copolymer of the present invention preferably has a charge density between about 25% and 75% and a molecular weight of between 8 million and 28 million:

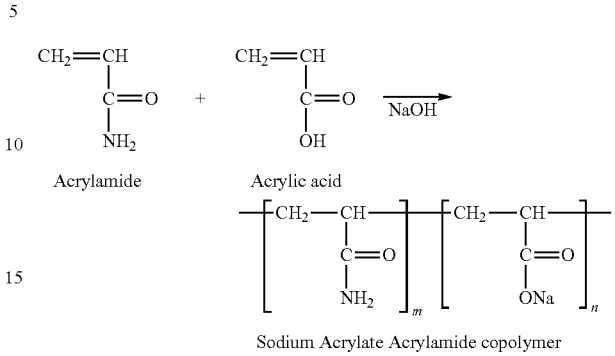

Acrylamide   Acrylic acid

Sodium Acrylate Acrylamide copolymer

In yet another embodiment of the present invention, the polymer is Acrylamide polymer with N,N,N-trimethyl-2-[1-oxo-2-propenyl]oxy Ethanaminium chloride, also listed as Acrylamide/Ethanaminium,N,N,N-trimethyl-2-((1-oxo-2-propenyl)oxy)-, chloride copolymer having a cationic charge density of between about 4% to about 12% and a molecular weight between about 4,000,000 and about 10,000,000.

The catalyst in the present invention may be sodium hydroxide or potassium hydroxide added at about 0.5%-1.5% by weight of the feed source resulting in a reaction pH of about 8.5 to about 9.5. The catalyst combines with the methanol to produce sodium methylate or potassium methylate which reacts with the triglycerides to produce methyl ester and glycerin.

The incorporation of the polymer causes the precipitation of the glycerin to take place at a faster rate than disclosed in the current art. This separation may occur within about two to about 4 hours.

In another embodiment of the present invention process, the separated methyl ester is passed through a dry desiccant and ion exchange resin such as Purolite® PD 206 or Purolite® D9957 to remove residual glycerin, trace methanol and water as well as salts, catalysts, and soaps from crude biodiesel.

Centrifuging the product mixture may additionally be desirable to further enhance the speed of the separation between the methyl ester and glycerin.

FIG. 1 represents an embodiment of the biodiesel process of the present invention comprising mixing methanol with a catalyst, such as sodium hydroxide or potassium hydroxide, then mixing with the triglyceride feed source in a heated reaction vessel. This is then followed by blending the polymer with the product mixture in a heated vessel. The product mixture is allowed to settle wherein the glycerin fraction precipitates by gravity and separates from the methyl ester fraction. If needed, the methyl ester is subsequently washed with a weak acid then washed with water to remove impurities. The water wash may be decanted and any residual water is removed by distillation.

Figure 2:
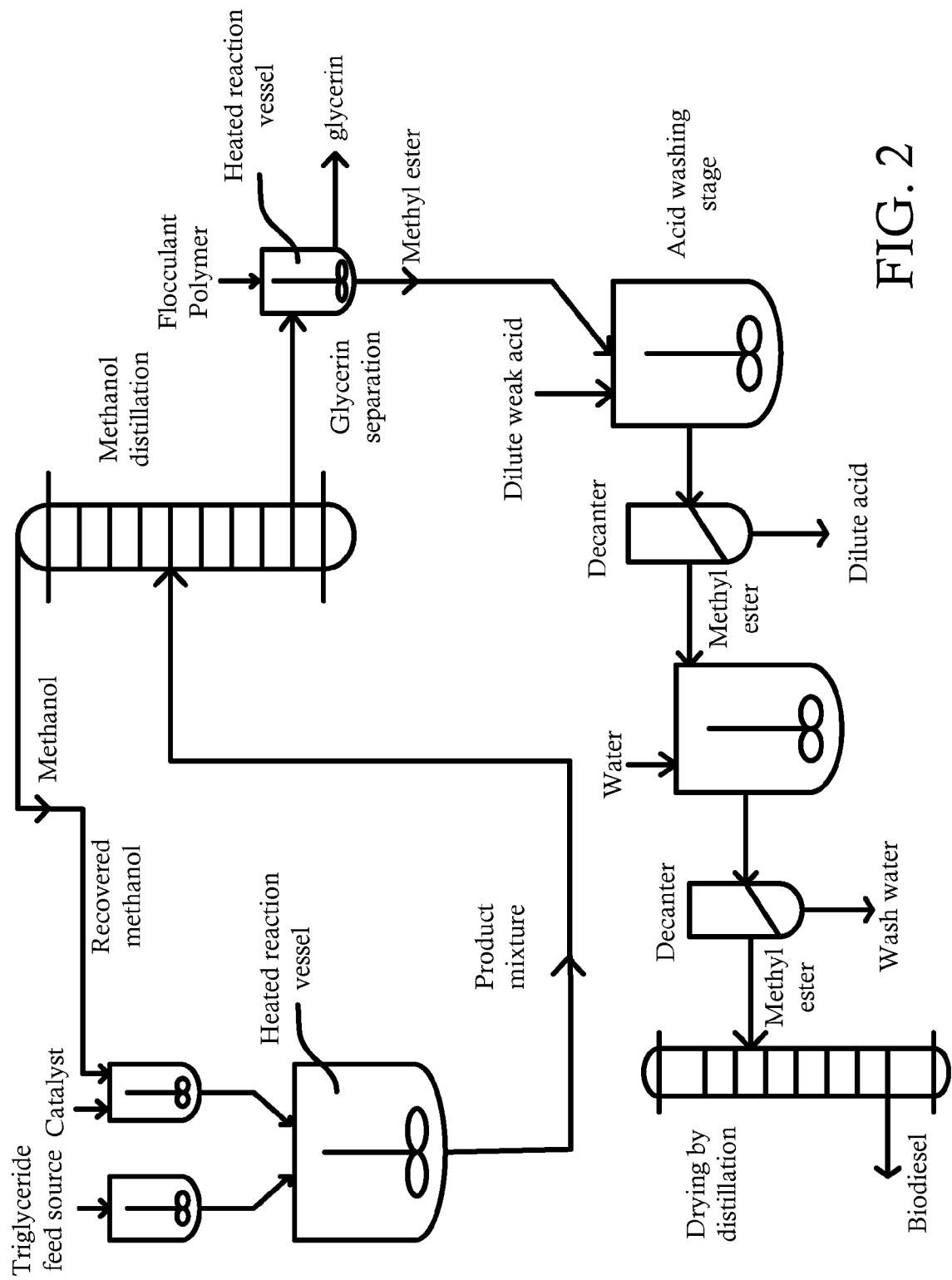
FIG. 2 is a schematic of a biodiesel process according to another embodiment of the present invention.

FIG. 2 represents an embodiment of the biodiesel process of the present invention comprising mixing methanol with a catalyst, such as sodium hydroxide or potassium hydroxide, then mixing with the triglyceride feed source in a heated reaction vessel. After the biodiesel reaction takes place, the methanol is distilled off the products mixture from which the recovered methanol is recycled back into the mixing and reaction vessel for reuse. This is then followed by blending the polymer with the product mixture in a heated vessel. The product mixture is allowed to settle wherein the glycerin fraction precipitates by gravity and separates from the methyl ester fraction. If needed, the methyl ester is subsequently washed with a weak acid then washed with water to remove impurities. The water wash may be decanted and any residual water is removed by distillation.

Figure 3:
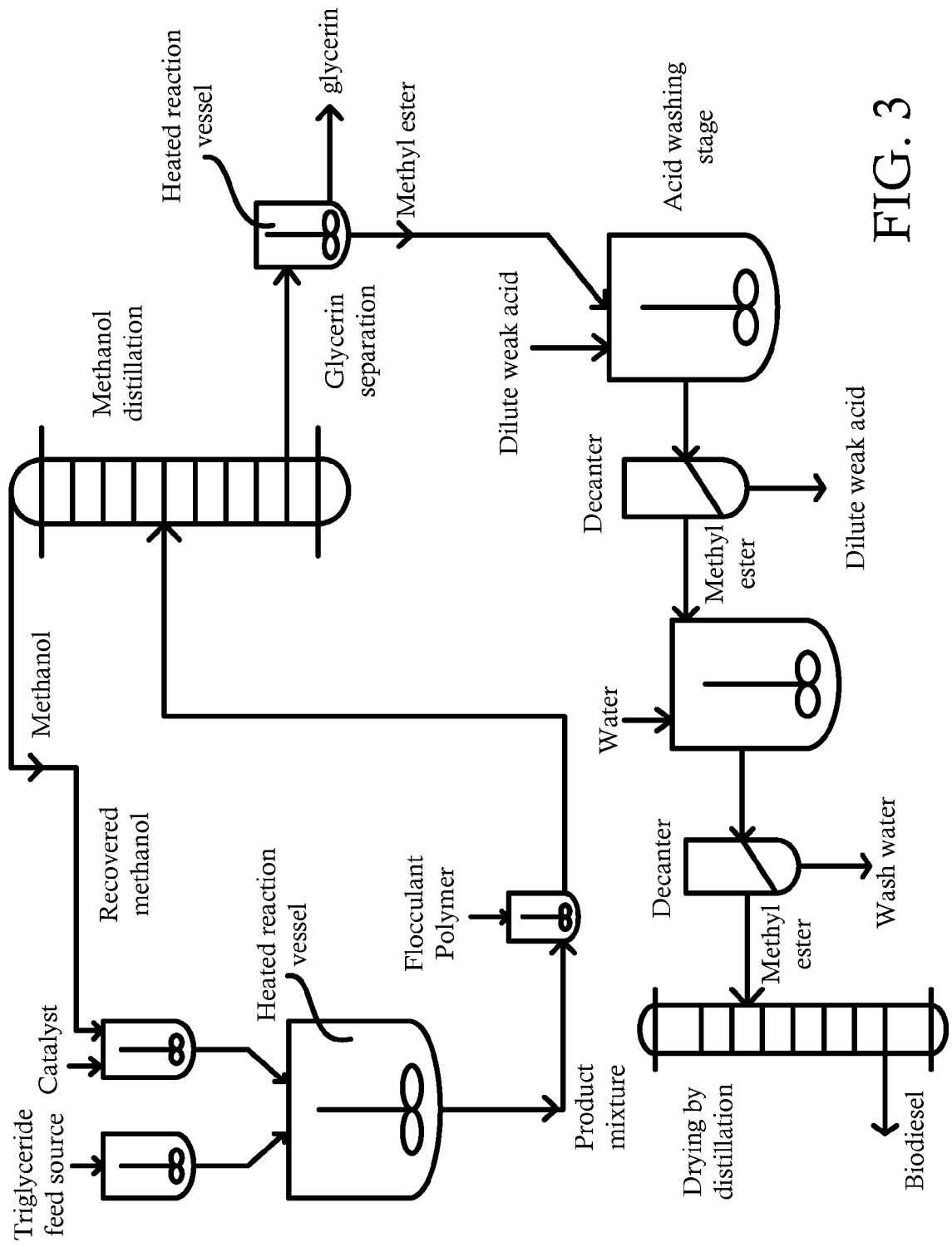
FIG. 3 is a schematic of a biodiesel process according to yet another embodiment of the present invention.

Referring to FIG. 3, an embodiment for producing biodiesel comprises mixing methanol with a catalyst, such as sodium hydroxide or potassium hydroxide, then mixing with the triglyceride feed source in a heated reaction vessel. After the biodiesel reaction takes place, a polymer is mixed with the product mixture, followed by the distillation of the methanol from the product mixture, from which the recovered methanol is recycled back into the mixing and reaction vessel for reuse. The product mixture is allowed to settle wherein the glycerin fraction precipitates by gravity and separates from the methyl ester fraction. If needed, the methyl ester is subsequently washed with a weak acid then washed with water to remove impurities. The water wash may be decanted and any residual water is removed by distillation.

EXAMPLES

In the following examples, 1000 cc of a triglyceride feed source was reacted with 200 cc of methanol and sodium hydroxide catalyst. A polymer was blended with the reactants mixture of methanol, catalyst and triglyceride feed source. The total percent glycerin in the methyl ester including free and bound glycerin was determined by subjecting the methyl ester to a temperature below 32° C. and observing any precipitated deposits at the bottom of the beaker. The absence of any deposits indicated that the total percent glycerin in the methyl ester was less than 0.21%. The reaction conditions and outcomes were as follows:

Example 1

Conditions

Triglyceride feed source: sunflower oil
Feed source pretreatment: none
% Fatty acids in the feed source: 0.06
Process:
Methanol: 200 cc
Catalyst: Sodium hydroxide added at 0.9% by weight
pH: 9
Reaction temperature: 45° C.
Reaction time: 40 minutes
Polymer: poly-diallyldimethyl-ammonium chloride
Polymer application rate: 15 parts per million by weight of the feed source
Polymer mixing time: 10 minutes
Separation temperature: 70° C.
Results
Separation time: 3 hours
% total glycerin in the methyl ester: less than 0.21%

Example 2

Conditions

Triglyceride feed source: canola oil
Feed source pretreatment: none
% Fatty acids in the feed source: 0.06
Process:
Methanol: 200 cc
Catalyst: Sodium hydroxide added at 0.9% by weight
pH: 9
Reaction temperature: 45° C.
Reaction time: 40 minutes
Polymer: poly-diallyldimethyl-ammonium chloride
Polymer application rate: 15 parts per million by weight of the feed source
Polymer mixing time: 10 minutes
Separation temperature: 70° C.
Results
Separation time: 2 hours
% glycerin in the methyl ester: less than 0.21

Example 3

Conditions

Triglyceride feed source: fried oil
Feed source pretreatment: none
% Fatty acids in the feed source: 0.02%
Process:
Methanol: 200 cc
Catalyst: Sodium hydroxide added at 1.1% by weight
pH: 9.5
Reaction temperature: 45° C.
Reaction time: 40 minutes
Polymer: polydicyandiamide
Polymer application rate: 15 parts per million by weight of the feed source
Polymer mixing time: 10 minutes
Separation temperature: 70° C.
Results
Separation time: 3 hours
% glycerin in the methyl ester: less than 0.21%

Example 4

Conditions

Triglyceride feed source: soybean oil
Feed source pretreatment: none
% Fatty acids in the feed source: 0.07
Process:
Methanol: 200 cc
Catalyst: Sodium hydroxide added at 0.7% by weight
pH: 9
Reaction temperature: 45° C.
Reaction time: 40 minutes
Polymer: polydicyandiamide
Polymer application rate: 5 parts per million by weight of the feed source
Polymer mixing time: 10 minutes
Separation temperature: 70° C.
Results
Separation time: 2 hours
% glycerin in the methyl ester: less than 0.21

Example 5

Conditions

Triglyceride feed source: cotton seed oil
Feed source pretreatment: none
% Fatty acids in the feed source: 0.09
Process:
Methanol: 200 cc
Catalyst: Sodium hydroxide added at 1% by weight
pH: 9
Reaction temperature: 45° C.
Reaction time: 40 minutes Polymer: polydicyandiamide
Polymer application rate: 15 parts per million by weight of the feed source
Polymer mixing time: 10 minutes
Separation temperature: 70° C.
Results
Separation time: 3 hours
% glycerin in the methyl ester: less than 0.21

We claim:

1. A method for the manufacture of methyl ester and for the separation of the methyl ester from glycerin at an enhanced rate and reduced number of process steps, said process comprising:
    providing a feed source containing triglyceride, said feed source being substantially water free;
    blending an alcohol and a catalyst with the feed source to produce a reactant mixture comprising of alcohol, pretreated feed source and catalyst, said reactant mixture being substantially water free;
    blending a polymer with the reactant mixture, said polymer being selected from the group consisting of; Polydimethylamine-Epichlorohydrin having a cationic charge density of between about 40% and about 60% and a molecular weight of between about 10,000 and about 1,000,000; Poly-Diallyldimethyl-Ammonium Chloride having a cationic charge density of between about 40% and about 60% and having a molecular weight between about 10,000 and about 1,000,000; Acrylamide/Ethanaminium,N,N,N-trimethyl-2-((1-oxo-2-propenyl)oxy)-chloride copolymer having a cationic charge density of between about 4% to about 12% and a molecular weight between about 4,000,000 and about 10,000,000; Polydicyandiamide having a cationic charge density of between about 40% and about 60% and having a molecular weight of between about 3,000 and about 150,000; and Sodium Acrylate Acrylamide copolymer having an anionic charge density of between about 25% and about 75% and a molecular weight between about 8,000,000 and about 28,000,000, and combinations thereof;
    heating the reactant mixture to a predetermined reaction temperature;
    reacting the reactant mixture in a substantially non-polar and water free environment for a predetermined reaction time to produce a product mixture comprising of methyl ester, glycerin, alcohol and catalyst;
    heating the product mixture to a predetermined separation temperature;
    precipitating a glycerin fraction from a methyl ester fraction;
    separating the glycerin fraction from the methyl ester fraction;
    recovering the methyl ester fraction; and
    recovering the glycerin fraction.

2. The method of claim 1, wherein a sufficient amount of catalyst is added to adjust the reactant mixture to a predetermined pH.

3. The method of claim 2, wherein the predetermined pH is in a range of about 8.5 and 9.5.

4. The method of claim 1, wherein the catalyst is sodium hydroxide.

5. The method of claim 1, wherein the catalyst is potassium hydroxide.

6. The method of claim 1 further comprising:
    separating the methanol from the product mixture and recovering a separated methanol stream; and
    reusing the separated methanol stream in subsequent process steps.

7. The method of claim 6 further comprising:
    washing the methyl ester fraction with acid;
    washing the methyl ester fraction with water;
    separating a residual acid wash and wash water from the methyl ester fraction; and
    passing the methyl ester through a dry desiccant and ion exchange resin.

8. The method of claim 1, wherein separating the glycerin fraction from the methyl ester fraction comprises providing a predetermined time period for the product mixture to separate into two phases by gravity.

9. The method of claim 1, wherein the alcohol comprises methanol.

10. The method of claim 1, wherein the polymer is blended with the product mixture at an amount of about 0.5 parts per million to about 100 parts per million by weight of the feed source.

11. The method of claim 10, wherein the polymer is blended with the product mixture at an amount of about 5 parts per million to about 25 parts per million by weight of the feed source.

12. The method of claim 1, wherein the predetermined reaction temperature is in a range between about 25° C. and about 50° C.

13. The method of claim 12, wherein the predetermined reaction temperature is in a range between about 35° C. and about 45° C.

14. The method of claim 1, wherein the predetermined separation temperature is in a range between about 40° C. and about 80° C.

15. The method of claim 14, wherein the predetermined separation temperature is in a range between about 60° C. and about 70° C.

16. The method of claim 1 further comprising centrifuging the product mixture.

17. The method of claim 1, wherein the predetermined reaction time ranges from about 20 minutes to about 60 minutes.

18. The method of claim 1, wherein the predetermined precipitation time ranges from about 2 hours to about 4 hours.

19. The method of claim 1 further comprising pre-treating the feed source containing triglyceride.

* * * * *